United States Patent [19]

Anderson et al.

[11] Patent Number: 5,610,708

[45] Date of Patent: *Mar. 11, 1997

[54] ANALYTICAL SENSOR USING GRATING LIGHT REFLECTION SPECTROSCOPY

[75] Inventors: Brian Anderson, Renton; Anatol Brodsky; Lloyd Burgess, both of Seattle, all of Wash.

[73] Assignee: University of Washington, Seattle, Wash.

[*] Notice: The term of this patent shall not extend beyond the expiration date of Pat. No. 5,502,560.

[21] Appl. No.: 551,525

[22] Filed: Nov. 1, 1995

Related U.S. Application Data

[63] Continuation of Ser. No. 279,473, Jul. 22, 1994, Pat. No. 5,502,560.

[51] Int. Cl.$^6$ .................................................. G01N 21/41
[52] U.S. Cl. ........................................................ 356/128
[58] Field of Search ................................. 356/128, 300, 356/326, 328

[56] References Cited

U.S. PATENT DOCUMENTS

| | | | |
|---|---|---|---|
| 3,702,736 | 11/1972 | Coggeshall | 356/328 |
| 4,436,420 | 3/1984 | Depp et al. | 356/128 |
| 4,715,715 | 12/1987 | Howarth et al. | 356/402 |
| 5,502,560 | 3/1996 | Anderson et al. | 356/128 |

FOREIGN PATENT DOCUMENTS

| 2141223 | 12/1984 | United Kingdom | 356/128 |
|---|---|---|---|

*Primary Examiner*—F. L. Evans
*Attorney, Agent, or Firm*—Christensen, O'Connor, Johnson & Kindness

[57] ABSTRACT

A optical analytical method and apparatus for measuring concentrations of materials in liquids and gases is described. The method is based upon measurements of light reflection from diffraction gratings in contact with the sample. Features in the reflection spectrum are directly related to the complex dielectric constant of the sample solution. By examining the reflection spectrum, the concentration of materials in the liquid or gas can be determined.

28 Claims, 8 Drawing Sheets

ANALYTICAL SENSOR USING GRATING LIGHT REFLECTION SPECTROSCOPY

This is a continuation of the prior application Ser. No. 08/279,473, filed Jul. 22, 1994, now U.S. Pat. No. 5,502,560, the benefit of the filing date of which are hereby claimed under 35 U.S.C. § 120.

FIELD OF THE INVENTION

The present invention relates to analytical sensors and, more particularly, a sensor that uses grating light reflection spectroscopy to determine the concentration of a material in liquids or gases.

BACKGROUND OF THE INVENTION

In recently published articles and patents there were described a number of methods for measuring bulk fluid compositions in statics and flow by visible light reflection characteristics from the optically inhomogeneous wall of a fluid containing vessel. Surface Plasmon Spectroscopy (SPS) on gratings and randomly rough surfaces has proven to be especially sensitive to fluid composition near the wall. See M. J. Jory, P. S. Vukusic, J. R. Sambles, *Sensors and Actuators B: Chemical*, 17, 203–209 (1994). It has been shown that SPS combined with electrochemical modulation techniques allow for the determination of relative concentrations of surface active species as low as $10^{-15}$ to $10^{14}$M. See A. M. Brodsky, M. Urbach, *Sov. Phys. Uspechi*, 132, 413 (1982).

SPS techniques in general have a number of inherent drawbacks when used as analytical sensing techniques. For instance, the metal dielectric interface that is necessary for surface plasmon generation must be chosen carefully. As only a limited number of metals (gold, silver) are available for the SPS, the technique is limited to environments that will not corrode or destroy the surface plasmon generation medium. In contrast, the technique described herein, termed Grating Light Reflection Spectroscopy (GLRS), relies on an optical phenomenon that requires only a sufficient dielectric difference between the substrate and "sensing" layers. Thus, any combination of substrate and grating materials with sufficient dielectric difference will suffice, allowing for sensing in environments that would preclude the use of SPS.

Additionally, the surface sensitivity associated with SPS techniques make them unstable for real world analytical applications as the bulk determinations of solutions would be unattainable in the presence of surface active analytes. The techniques described herein proves to be relatively insensitive to surface active species. Although, here, we have not shown this effect experimentally, the mathematics described below indicate a relative surface insensitivity.

SUMMARY OF THE INVENTION

A optical analytical method and apparatus for measuring concentrations of materials in liquids and gases is described. The method is based upon measurements of light reflection from diffraction gratings in contact with the sample. Features in the reflection spectrum are directly related to the complex dielectric constant of the sample solution. By examining the reflection spectrum, the concentration of materials in the liquid or gas can be determined.

In particular, the intensity and phase modulations of the reflection spectrum are examined to determine the bulk dielectric properties of the solution or gas in contact with the diffraction grating.

BRIEF DESCRIPTION OF THE DRAWINGS

The foregoing aspects and many of the attendant advantages of this invention will become more readily appreciated as the same becomes better understood by reference to the following detailed description, when taken in conjunction with the accompanying drawings, wherein.

DETAILED DESCRIPTION OF THE PREFERRED EMBODIMENT

Figure 1:
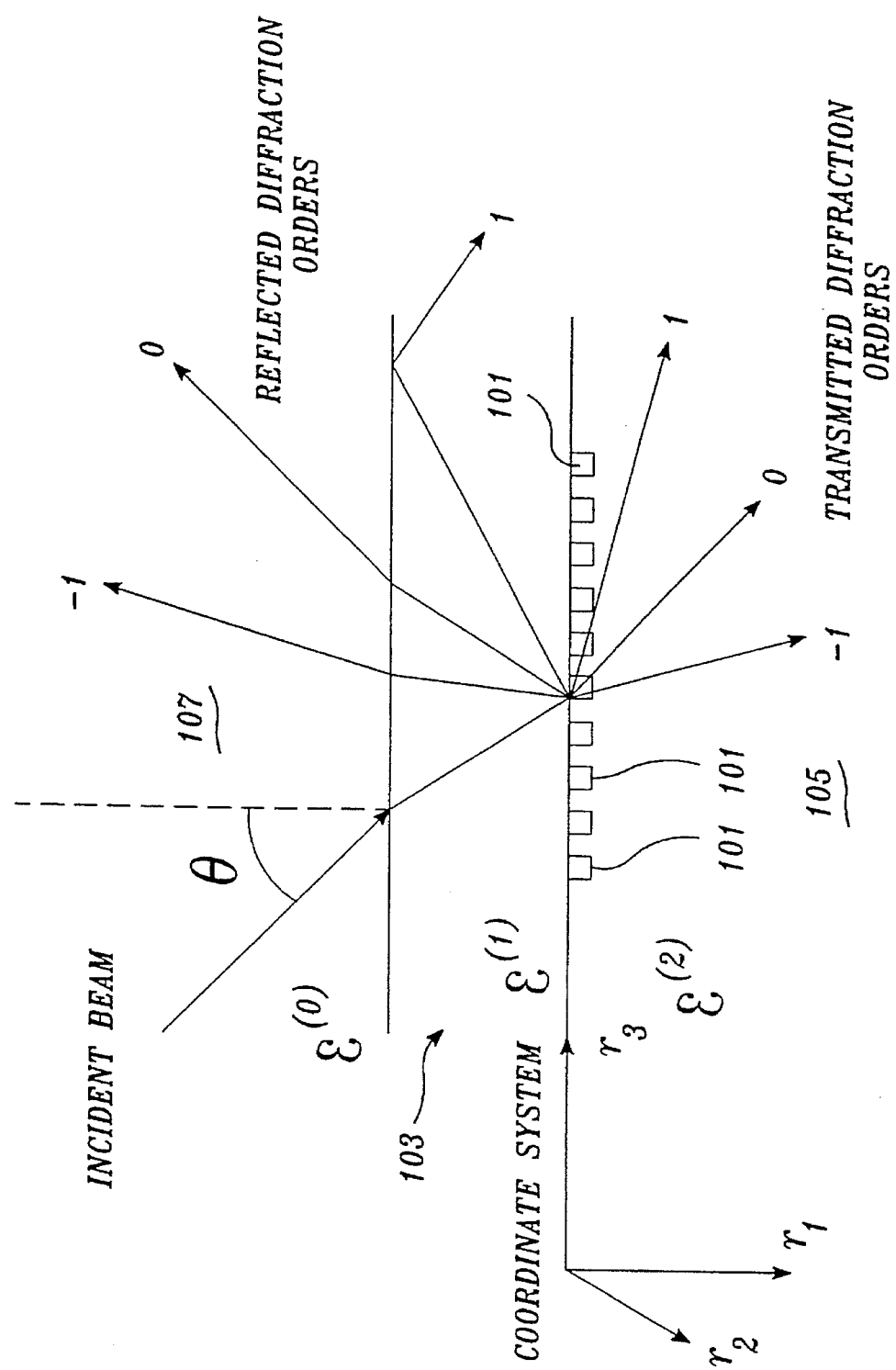
FIG. 1 is a schematic diagram of grating light reflection spectroscopy (GLRS) on a planar wall.

The detailed description is organized as follows. In Section I the theoretical underpinnings of GLRS is described. In Section II, the experimental device and procedures is described. In Section III, the experimental results and analysis for ethanol-water mixtures is presented. In Section IV, possible applications of the present invention is described.

I. Theoretical

The present invention relies on the propagation modulation of a light beam that is incident on a diffraction grating 101 fabricated of metal lines on a dielectric 103, in this case chrome and glass. Certain features in the diffracted reflection spectra, namely intensity and phase modulations, are directly related to bulk dielectric properties of the solution 105 in contact with the grating (see FIG. 1). The external media 107 and the dieletric 103 are characterized by dielectric functions $\epsilon^{(0)}(\omega)$ and $\epsilon^{(1)}(\omega)$, respectively, where $\omega$ in the arguments designates the frequency dependence of the dielectric function. As the external medium for these experiments is air, $\epsilon^{(0)}(\omega)$ is taken to be unity for this theoretical development. The solution of 105 is characterized by a dielectric function $\epsilon^{(2)}(\omega)$ and supports different transmitted beams. The emergence of reflected and transmitted beams with m≠0, where m is the diffraction order $0, \pm 1, \pm 2 \ldots$, is the result of diffraction from the grating structure on the bottom of the substrate and in contact with the solution. For the sake of notational consistency, the superscripts on the wavevector or dielectric function symbols in the following equations refers to the medium, as designated above by (0), (1), (2) with (0) being the external media 107, (1) being the substrate 103, and (2) being the solution 105. Subscripts in the equations refer to the cartesian coordinate component, with 1 being the normal to the incident plane (see FIG. 1). The wave vectors $\vec{k}^{(i)}(i=0,1,2)$ in different media have normal $\vec{k}_1^{(i)}$ and parallel $\vec{k}_2^{(i)}$ components to the surfaces which are connected by the following condition:

$$\vec{k}^{(i)2} = \vec{k}_1^{(i)2} + \vec{k}_2^{(i)2} = \frac{\omega^2}{c^2} \epsilon^{(i)}(\omega) \tag{1}$$

where c is the speed of light. If the grating is strictly periodic then the parallel components $\vec{k}_2^{(i)}(m)$ of the wave vectors corresponding to different diffraction orders, m, due to momentum conservation laws, are subject to the following constraint:

$$\vec{k}_2(0,1,2)(m) = \frac{\omega}{c} \sin\theta\, m\, \frac{2\pi}{a} \;;\; m = 0, \pm 1, \pm 2 \tag{2}$$

where $\alpha$ is the grating period, $\theta$ is the incidence angle, and m in the argument of the wavevector denotes the difference wavevector associated with each diffracted order. As it follows from equations (1) and (2) the normal components $\vec{k}_1^{(2)}(m)$ of the wave vector in medium 2 are equal to:

$$k_1^{(2)}(m) = \sqrt{\frac{\omega^2}{c^2} \epsilon^{(2)}(\omega) - \left(\frac{\omega}{c}\sin\theta + m\frac{2\pi}{a}\right)^2} \tag{3}$$

If the value of $Re\epsilon^{(2)}(\omega)$, (Re and Im denoting the real and imaginary parts of the complex dielectric function respectively), is changing composition of the solution of interest (medium 2) or due to changing frequency $\omega$ there exists for some value $m_{cr}$, a critical diffraction order, a threshold where the function $$\delta_{m_\alpha} = Re(\epsilon^{(2)}(\omega)) - \left(\sin\theta + \frac{m_{cr}\lambda}{a}\right)^2, \lambda = \frac{2\pi c}{\omega} \tag{4}$$

passes through zero and becomes negative with further decline or $Re(\epsilon^{(2)}(\omega))$. Here, $\lambda$ is the free space wavelength of the incident radiation. For the case of $Im(\epsilon^{(2)}(\omega)) < Re(\epsilon^{(2)}(\omega))$ we will observe specific singularities in the behavior of reflected light. The important point is that the positions of such singularities, $\delta m_{cr} = 0$, and the functional dependence on $\delta m_{cr}$ in the interval where $\delta m_{cr}$ is small, $|\delta m_{cr}| \ll 1$, are dependent only on the bulk properties of the solution at distances from the solution-grating interface on the order of a few wavelengths. The physical origin of such singularities can be interpreted as follows. The intensity $I(\vec{r},m)$ of the light corresponding to the mth diffraction order in medium (2) is proportional to:

$$I(\vec{r}, m) \sim (\vec{E}^{(2)}(\vec{r}, m) \cdot \vec{E}^{(2)*}(\vec{r}, m)) \text{ for } r_1 > 0 \tag{5}$$

$\vec{r}$ is the direction vector for the propagation order as defined by the coordinate system in FIG. 1 and the asterisk denotes the complex conjugate of the quantity $\vec{E}^{(2)}(\vec{r},m)$. Where $\vec{E}^{(2)}(\vec{r}, m)$ is the corresponding complex amplitude of the transmitted beam. In the case of transparent media $(Im(\epsilon^{(2)}(\omega))=0)$:

$$I(\vec{r}, m)_{cr} \sim (e^{i\sqrt{\delta_m} \cdot r_1} \cdot e^{-i\sqrt{\delta_m} \cdot r_1}) \sim \text{constant for } \delta_{m_{cr}} > 0 \tag{6}$$

$$I(\vec{r}, m)_{cr} \sim (e^{i\sqrt{|\delta_m|} \cdot r_1} \cdot e^{-i\sqrt{|\delta_m|} \cdot r_1}) \sim e^{-2\sqrt{|\delta_m|} \cdot r_1} \text{ for } \delta_{m_{cr}} \leq 0 \tag{7}$$

The dependence of transmitted light on the distance from the surface has been drastically changed as $\delta m_{cr}$ becomes negative. At $\delta m_{cr} = 0$, the intensity $\vec{I}(\vec{r}, n_{cr})$ remains constant in infinite volume but begins to diminish with further decline of $\delta m_{cr}$. This volume becomes finite if the imaginary part of the dielectric constant is nonzero $(Im\epsilon^{(2)}(\omega) \neq 0)$, or, in other words, there is an absorbing species in solution. A finite $(Im\epsilon^{(2)}(\omega))$ will to some extent smooth the singular behavior near $\delta m_{cr} > 0$. Nevertheless, if $$Im\epsilon^{(2)}(\omega) < |Re(\epsilon^{(2)}(\omega) - \epsilon^{(1)}(\omega)| \tag{8}$$

near the transmitted light thresholds, $\delta m_{cr} = 0$, the behavior of all reflected beams with different m will substantially change. Analytically, this behavior can be described by the following expressions for reflection coefficients $R^{(s,p)}(m)$, for s- and p-polarized light (transverse electric and transverse magnetic, respectively) in the interval of parameters in the threshold region ($\delta m_{cr}$ lies near zero):

$$\begin{aligned} R^{(s,p)}(m) &\cong C_1^{(s,p)}(m) + C_2^{(s,p)}(m)\sqrt{\frac{1}{2}\left(\sqrt{\delta_{m_\alpha}^2 + (Im\epsilon^{(2)})^2} - \delta_{m_\alpha}\right)} + \\ &\quad C_3^{(s,p)}(m)\sqrt{\frac{1}{2}\left(\sqrt{\delta_{m_\alpha}^2 + (Im\epsilon^{(2)})^2} + \delta_{m_\alpha}\right)} \\ &= C_1^{(s,p)}(m) + \begin{cases} C_2^{(s,p)}(m)\sqrt{|\delta_{m_\alpha}|} & \delta_{m_\alpha} \leq 0 \\ C_3^{(s,p)}(m)\sqrt{|\delta_{m_\alpha}|} & \text{for } \delta_{m_\alpha} > 0 \end{cases} \end{aligned} \tag{9}$$

as $Im\epsilon^{(2)} \to 0$ and for the phase of reflected light:

$$\begin{aligned} \alpha^{(s,p)}(m) &\cong C_4^{(s,p)}(m) + C_5^{(s,p)}(m)\sqrt{\frac{1}{2}\left(\sqrt{\delta_{m_\alpha}^2 + (Im\epsilon^{(2)})^2} - \delta_{m_\alpha}\right)} + \\ &\quad C_3^{(s,p)}(m)\sqrt{\frac{1}{2}\left(\sqrt{\delta_{m_\alpha}^2 + (Im\epsilon^{(2)})^2} + \delta_{m_\alpha}\right)} \\ &= C_4^{(s,p)}(m) + C_5(s,p)(m)\delta_{m_\alpha} \end{aligned} \tag{10}$$

as $Im\epsilon^{(2)} \to 0$ where parameters $C_{1,2,3,4,5}^{(s,p)}(m)$ are constants and $\alpha^{(s,p)}(n)$ corresponds to the phase of the reflected light. For $n\neq 0$, the constants $C_{1,2,3,4,5}^{(s,p)}(n)$ are related to the difference in dielectric constant between the grating lines (metal) and the substrate materials (glass). The important point is that the positions of singularities $\delta m_{cr}=0$ and the functional dependence on $\delta m_{cr}$ in the interval $\delta m_{cr}<1$ are dependent only on the bulk properties of the solution at distances from the solution-grating interface on the order of a few wavelengths. This means that this position, as well as the reflection coefficient's behavior in the vicinity of this position, in contrast to other properties of reflected light, will remain stable and unaffected by changing surface properties at distances less than $$\lambda = \frac{\omega}{c} Re(\epsilon^{(2)}).$$

II. Experimental

Figure 1A:
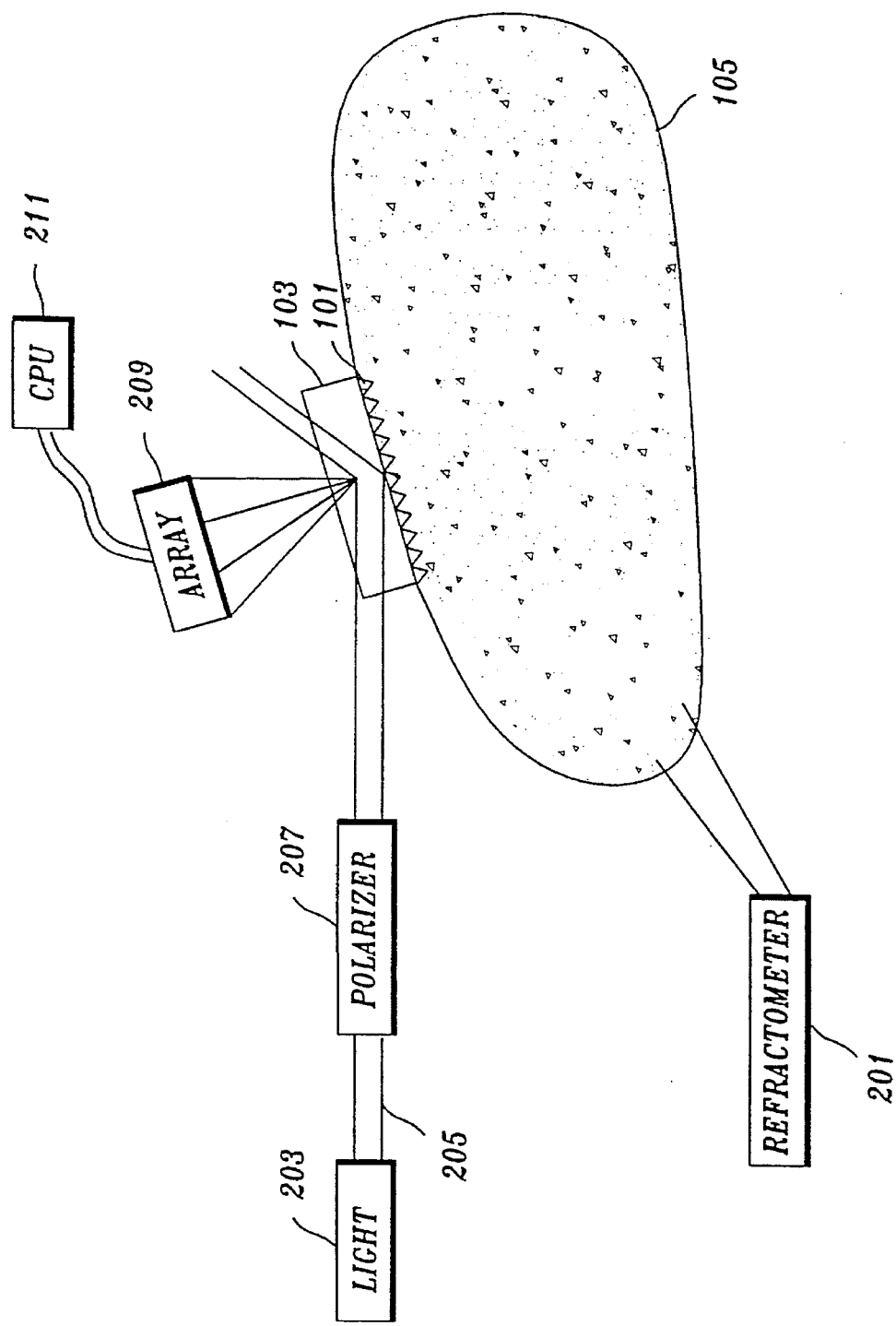
FIG. 1A is an illustration of an apparatus formed in accordance with the present invention.

Turning to FIG. 1A, a single diffraction grating 101 was fabricated in a high-reflective chrome mask layer (1000 angstrom thickness) deposited on a microscope slide 103. A Lloyd's mirror optical configuration was used to record interference fringes from an argon ion laser in a positive photoresist spin-coated on the slide. The resist was developed to the chrome layer, and then the chrome was wet chemically etched to the glass substrate, forming a transmission grating. The grating period was measured to be 0.84 microns with good uniformity and a sinusoidal surface profile.

Eleven ethanol solutions 105 were prepared in deionized water from absolute ethanol. The concentration range was 1% EtOH by volume to 50% EtOH by volume. This corresponds to a refractive index range from 1.331 to 1.3579 RI units. The refractive indices of the solutions were measured with an Abbé refractometer 201 (Bausch and Lomb) to ±0001 RI units at a wavelength of 589.3 nanometers and the dispersion was calculated, assuming normal dispersion in the visible region of the spectrum.

The white light source 203 for these experiments was a tungsten bulb with a DC voltage source that was coupled into a 140 micron silica fiber optic 205. The fiber output was collimated via a 40X microscope objective and polarized with a Glan Taylor polarizing prism 207. The collimated light was incident on the backside of the substrate, and thus passed through the glass to the grating. Here the grating acted as the dispersing element and the m=−1 reflected diffraction order was imaged on a 512 element fiber-optic window photodiode array 209 (EG&G Reticon). Approximately 175 nm were imaged on the diode array, and the image was calibrated via bandpass filters and exhibited a linear dependence of wavelength on diode number. The spot size of the beam was approximately 5 mm, and the diffracted light was focused on the detector with a 63 mm focal length achromat lens. The substrate itself was placed into a sandwich flow cell which was mounted on a positioning stage that allowed translational adjustment and angular control to ±0.083 degrees.

As stated above, the substrate was mounted into a sandwich flow cell and sealed with a silicone rubber gasket. The grating was in contact with the solution and the backside of the slide faced the optical train. The light that was collected on the photodiode array was reflected light, and thus did not pass through the solution. The optics were aligned such that a 37 degree coupling angle from normal was achieved. The polarization of the incident beam was chosen as transverse electric (TE), or transverse magnetic (TM).

Measurements were taken in a stop flow format in order to remove flow effects. Sample was introduced into the cell with a peristaltic pump, and flushing sequence was a combination of well-defined flow and stop flow steps in order to allow complete flushing to minimize contamination from previous runs. Data was collected as full array images at 5 second intervals, with 30 scans of the array taken for each solution. The solutions, numbered 1–11, were run in random order with a water reference run between each alcohol solution.

Each 30 scan block was placed into a Matlab™ (Mathworks, Inc.) 211 file and averaged to obtain a single image for each solution run for calibration purposes. Each alcohol run was subtracted from its corresponding water blank, and this difference spectrum was the analytical signal that was used for Partial Least Squares (PLS) calibration. The individual spectra were then placed into a response matrix, and the refractive indices that were calculated from the Abbé refractomer dispersion measurements were used as the concentration matrix for the PLS calibration.

III. Experimental Results

Figure 2:
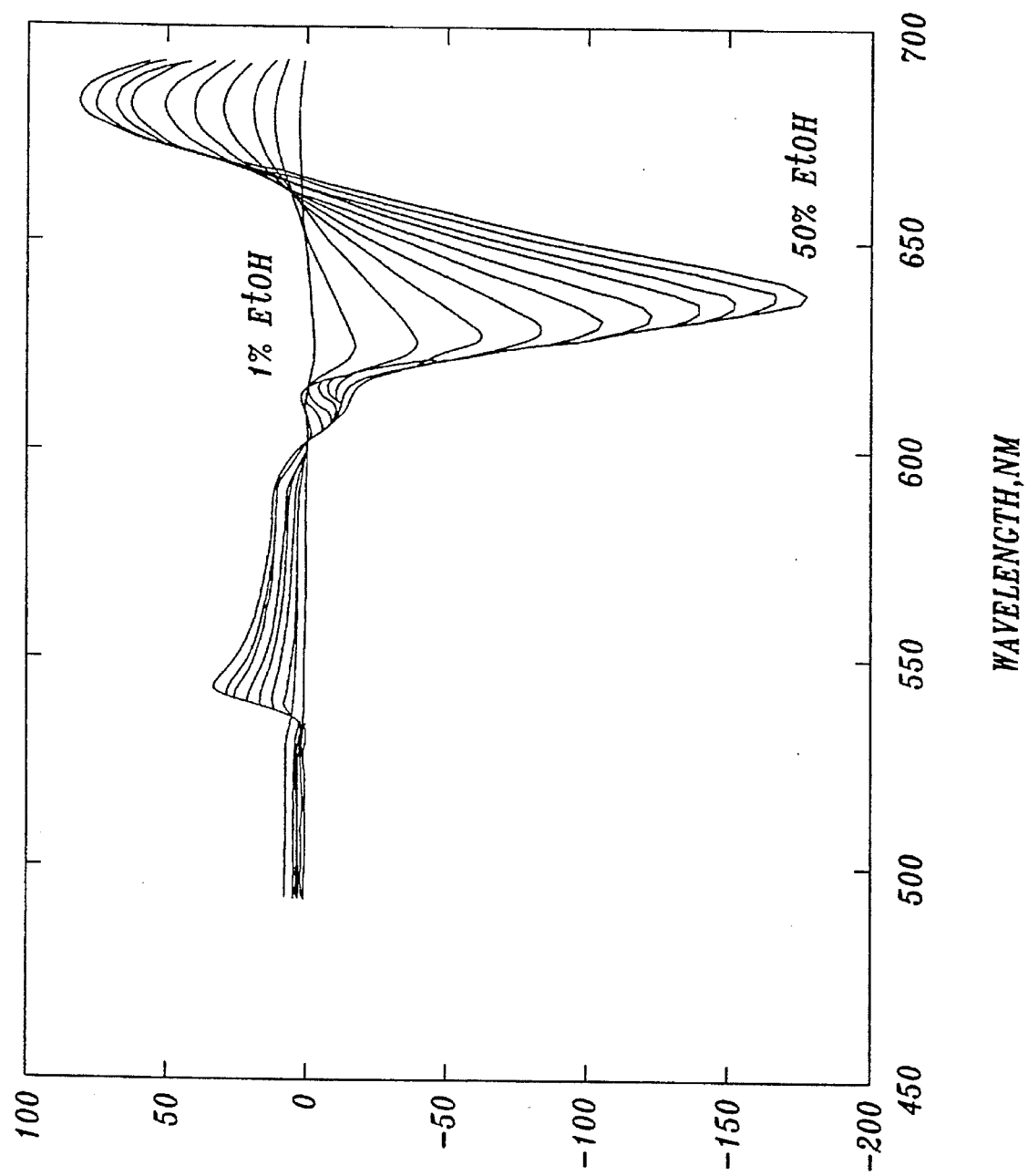
FIG. 2 is a graph of response reflection coefficient for TM polarization during grating reflection spectroscopy of EtOH solutions in water.
Figure 3:
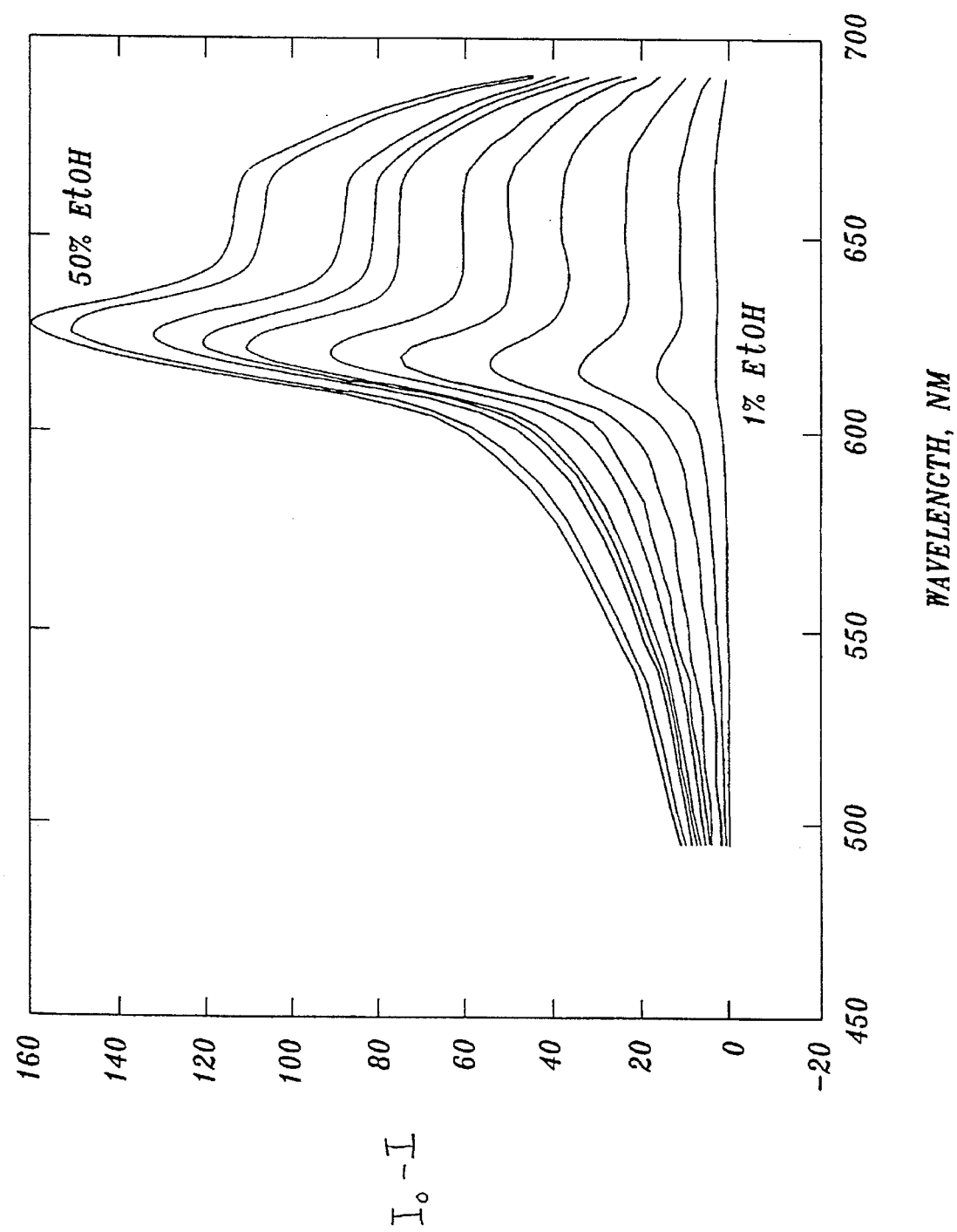
FIG. 3 is a graph of response reflection coefficient for TE polarization during grating reflection spectroscopy of EtOH solutions in water.
Figure 4:
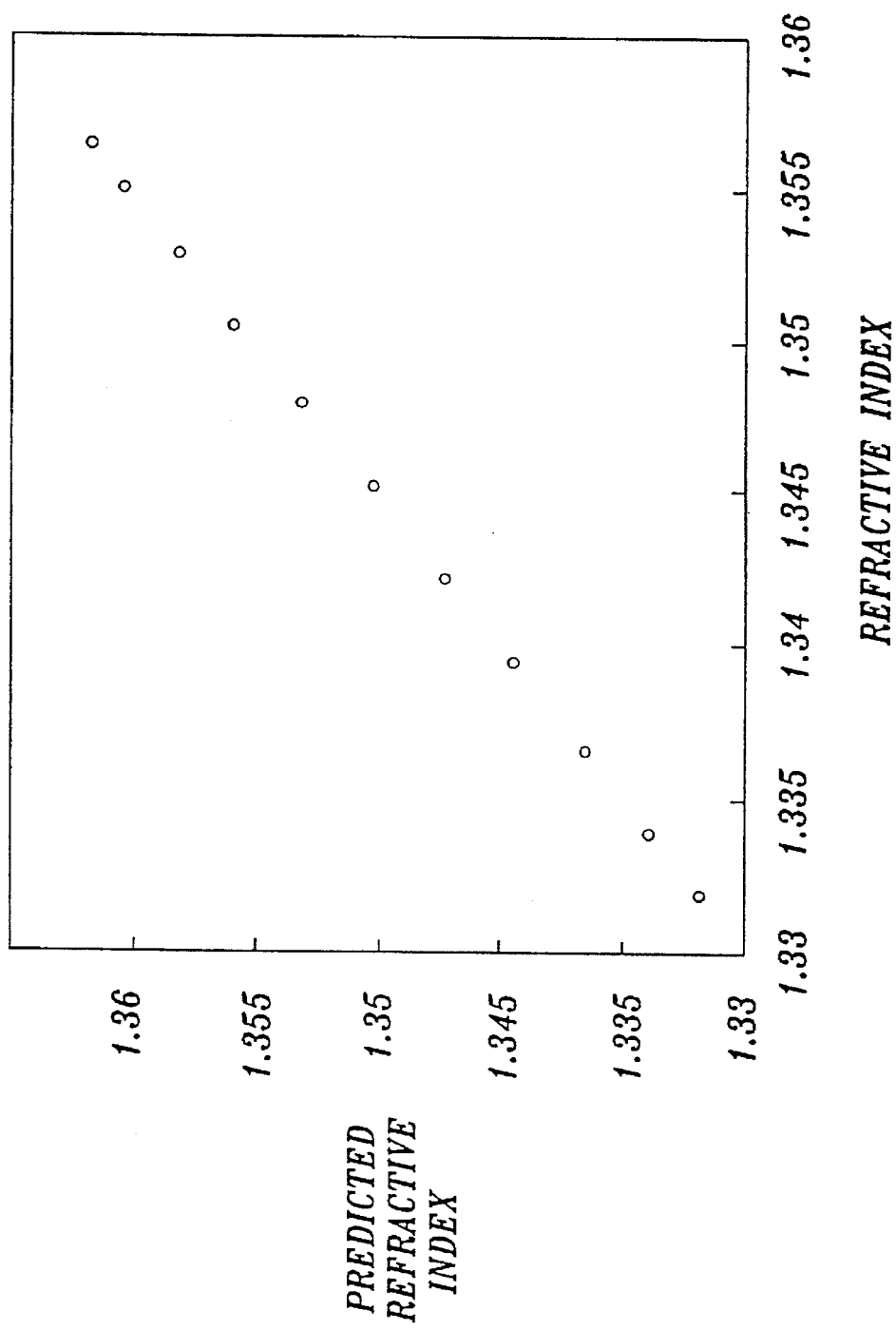
FIG. 4 is a graph of PLS prediction of refractive indices of EtOH solutions in water for TM polarization in a four factor model.
Figure 5:
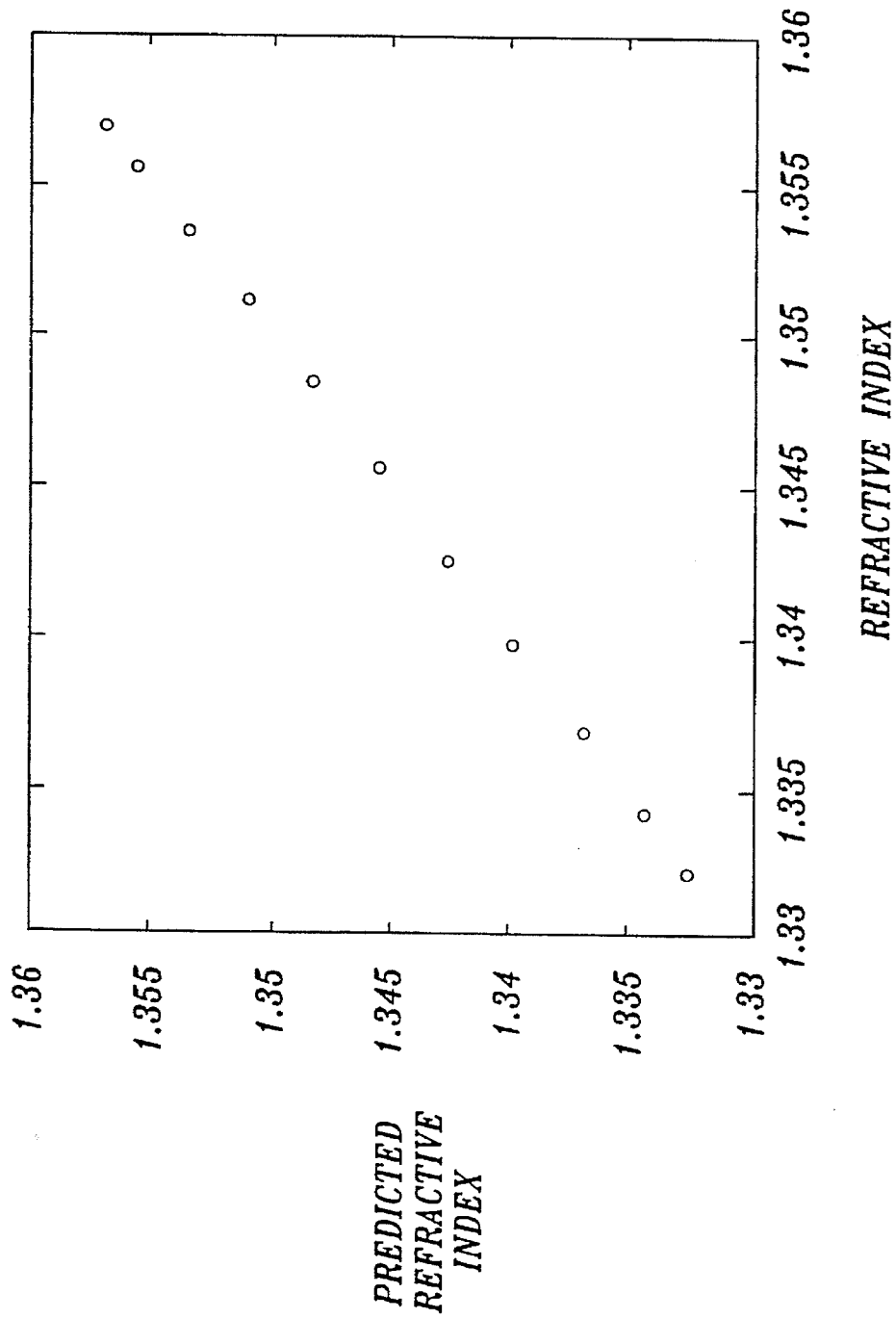
FIG. 5 is a graph of PLS prediction of refractive indices of EtOH solutions in water for TE polarization in a five factor model.

FIGS. 2 and 3 are the experimental reflection spectra for m=1 for TE and TM polarizations for the 11 solutions referenced to water. The plots show the dependence of the singularity position on dielectric constant of the solution. These spectra were loaded into the PLS algorithm, with measured refractive indices and dispersions used to calculate the refractive index for each solution at an average wavelength close to the singularity. For the TE polarization, the refractive index at 625 nm was used. For the TM polarization, the refractive index at 614 nanometers was used for the calibration. The difference in the position of the singularity for the different polarizations arises from the adjustment of the optical train between the two polarization experiments. Adjusting the polarizer effectively adjusts the incident angle. The calibration was also run using the alcohol concentrations for each solution in % vol/vol. EtOH in water. The calibration results are summarized in tables 1 and 2. The dependence of refractive index on EtOH concentration was calculated to a first approximation from a linear regression of the % EtOH and refractive indices at appropriate wavelengths in order to get a final error of prediction in terms of % EtOH. It was found that the calibration was an order of magnitude better for the TM polarization and comparable for the TE polarization when the refractive indices were used in the calibration. This is probably due to the information contained in the feature in the TM plot at around 545 nm, which might be another diffraction order singularity or an as yet unexplained optical effect. The relationship between the refractive index and concentration of each solution yields a limiting error of 0.188% EtOH RMS due to the uncertainty in the Abbe refractometer of ±0001 RI units. The TE RMSECV shows that this limiting value was reached, so this sensor has achieved an accuracy that is as good as the standard method used to make up the calibration. The prediction plots are for the lowest factor with RMSEVC of less than 0.0001 RI units, as a lower error is not statically significant. The prediction plots are shown in FIGS. 4 and 5.

TABLE 1

Root mean square error of cross validation values for calibration of the GLRS sensor for EtOH solutions for TM incident polarization.

| # of PLS Factors | RMSECV, %EtOH, calculated using %EtOH as calibration set | RMSECV, RI units, calculated using RI as calibration set | Calculated RMSECV from RI calibration set, in %EtOH units |
|---|---|---|---|
| 1 | 1.3050 | 0.000200 | 0.379 |
| 2 | 1.0600 | 0.000222 | 0.421 |
| 3 | 0.6317 | 0.000114 | 0.216 |
| 4 | 0.2811 | 0.000054 | 0.102 |
| 5 | 0.3526 | 0.000043 | 0.082 |

TABLE 2

Root mean square error of cross validation values for calibration of the GLRS sensor for EtOH solutions for TE incident polarization.

| # of PLS Factors | RMSECV, %EtOH, calculated using %EtOH as calibration set | RMSECV, RI units, calculated using RI as calibration set | Calculated RMSECV from RI calibration set, in %EtOH units |
|---|---|---|---|
| 1 | 1.2605 | 0.000585 | 1.110 |
| 2 | 0.7944 | 0.000343 | 0.651 |
| 3 | 0.8105 | 0.000376 | 0.714 |
| 4 | 0.2427 | 0.000106 | 0.201 |
| 5 | 0.2286 | 0.000097 | 0.184 |

Figure 6:
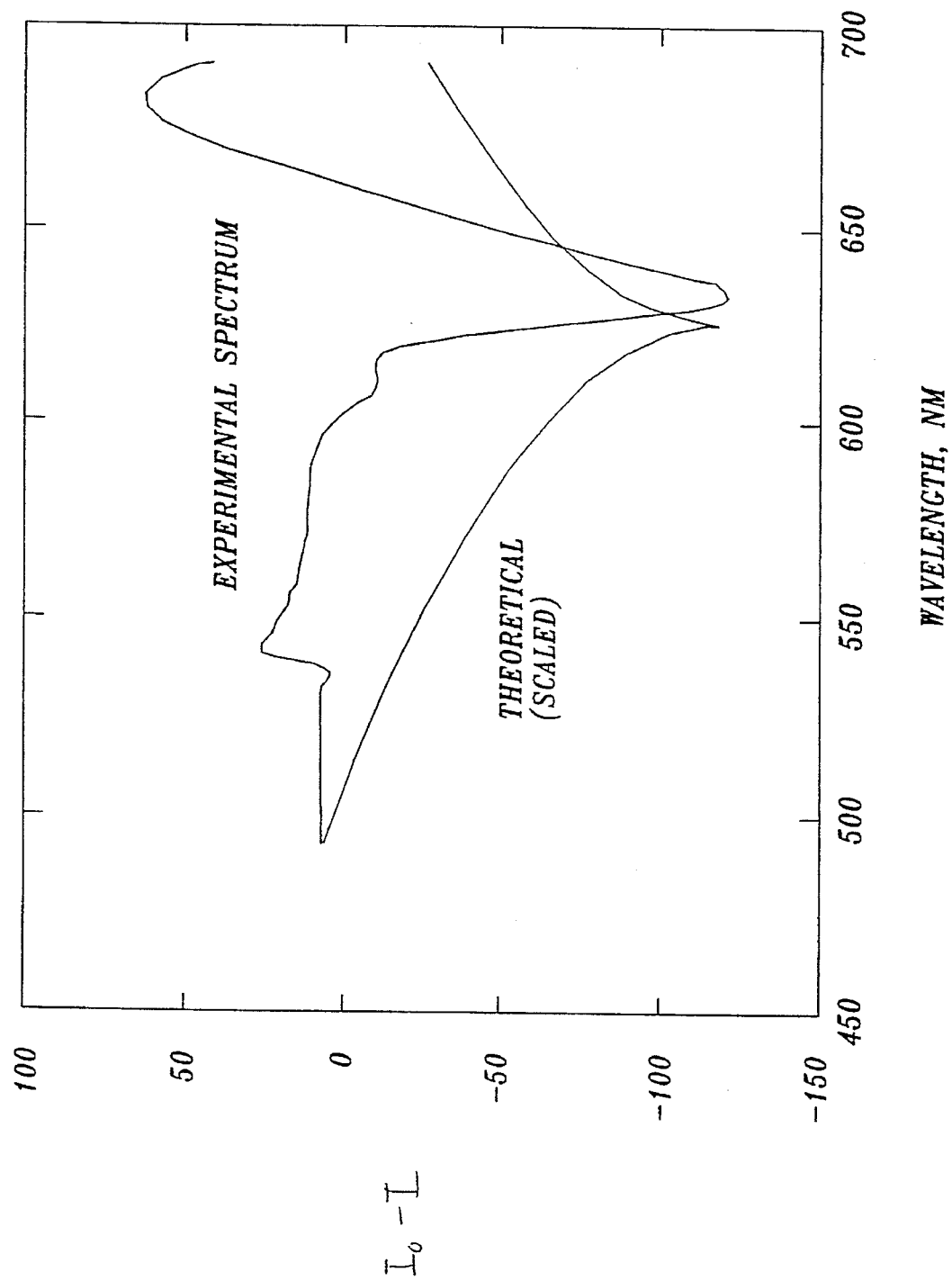
FIG. 6 is a graphical comparison of the theoretical position of a singularity with experimental spectrum for GLRS, TM polarization, and 30% EtOH solution.

The wavelength dependence of $\sqrt{|\delta_1|}$ was determined using the dispersion data obtained from the Abbe refractometer and plotted for the 30% EtOH solution, TM polarization, and plotted in FIG. 6. The important point to be made here is that the position of the singularity matches very closely with the minimum in the reflection coefficient plot, in the limit of experimental error and uncertainty. The detailed form of the reflection coefficient includes the constants mentioned in the introduction, but here we will not determine them as they must be determined empirically for each solution. Thus, only the position of the minimum in the theoretical plot is of value for comparison. The theory developed here is with regard to the region close to the singularity, and any fitting to the actual experimental curve at wavelengths removed from the vicinity of the singularity was not performed. The width of the minimum, according to Equation 9, is related to the imaginary part of the dielectric function. The theoretical plot assumes a value of zero for the imaginary part of the dielectric function. Thus, the shape of the theoretical curve at the singularity is much sharper than the experimental curve, as the experimental results indicate a non-zero dielectric function around the singularity. The offset of 7 nm between minima is due to experimental error in determining the grating period, coupling angle, and refractive index. This assumes that the grating lines are perpendicular to the plane of incidence. Deviation from this condition will result in spectral offset. Also, a one degree uncertainty in the coupling angle produces a 12 nm shift in the singularity position, and the difficulty in determining normal for the coupling angle reference is the most likely cause of the offset. However, the agreement in general form and position provides evidence that the theoretical predictions regarding the position of the singularity and the general form of the reflection spectrum are correct.

IV. Conclusion

Even the relatively rough experiments demonstrated the feasibility of this proposed method. The calibration of the device via chemometrics indicates the usefulness of this method as a first order chemical sensor, yielding a vector of data for each sample. For analytical purposes it is possible to use the dependence of the singularity positions on concentration as well as the form of the reflection and phase behavior near the singularities. If an absorbing species is present in solution in small amounts, the form of the reflection coefficient around the singularity will change. According to Equation 9 in the case of $\text{Im}\epsilon^{(2)}=0$ there must be a plateau in the dependence of $R_m(\delta_m)$ on $\delta_{m_{cr}}0$. Thus the concentration of absorbing species can be measured according to the width of the plateau in $R_m(\delta_{m_{cr}})$ dependency near $\delta_{m_{cr}}=0$ described by $\sqrt{\text{Im}\epsilon^{(2)}}$. By such methods it is possible, in principle, to measure relatively small concentrations of absorbing species. The obtained results show that the concentration sensitivity could be not less than $\text{Im}\epsilon^{(2)}=10^{-2}$.

As this is not a surface plasmon technique, there is no materials constraint regarding the metal used for the gratings. Thus, gratings may be fabricated in any metal. This gives wide latitude for performing analyses, as the properties of the metal may be chosen to impart selectively and exploit the dependence of the signal on dielectric differences between the metal and the substrate, thus making the grating an active chemical sensing region with which to perform the analyses.

Also, the relative insensitivity to surface absorbents of the position of the singularity will allow bulk analyses to be performed in a medium that would not be amenable to an ATR or SPS probe. This bulk determination coupled with the reflection basis of the system makes it ideal for chromatographic applications where the pathlength is insufficient to perform transmission spectroscopic measurements, as is the case with microbore chromatography.

As this is a reflection method, the analysis of average bulk properties in a highly scattering medium is possible. The signal would be dependent on the particle size and also on the homogeneity of the solution. This has application in processes or chemical systems that would not be suitable for transmission measurements.

Figure 1B:
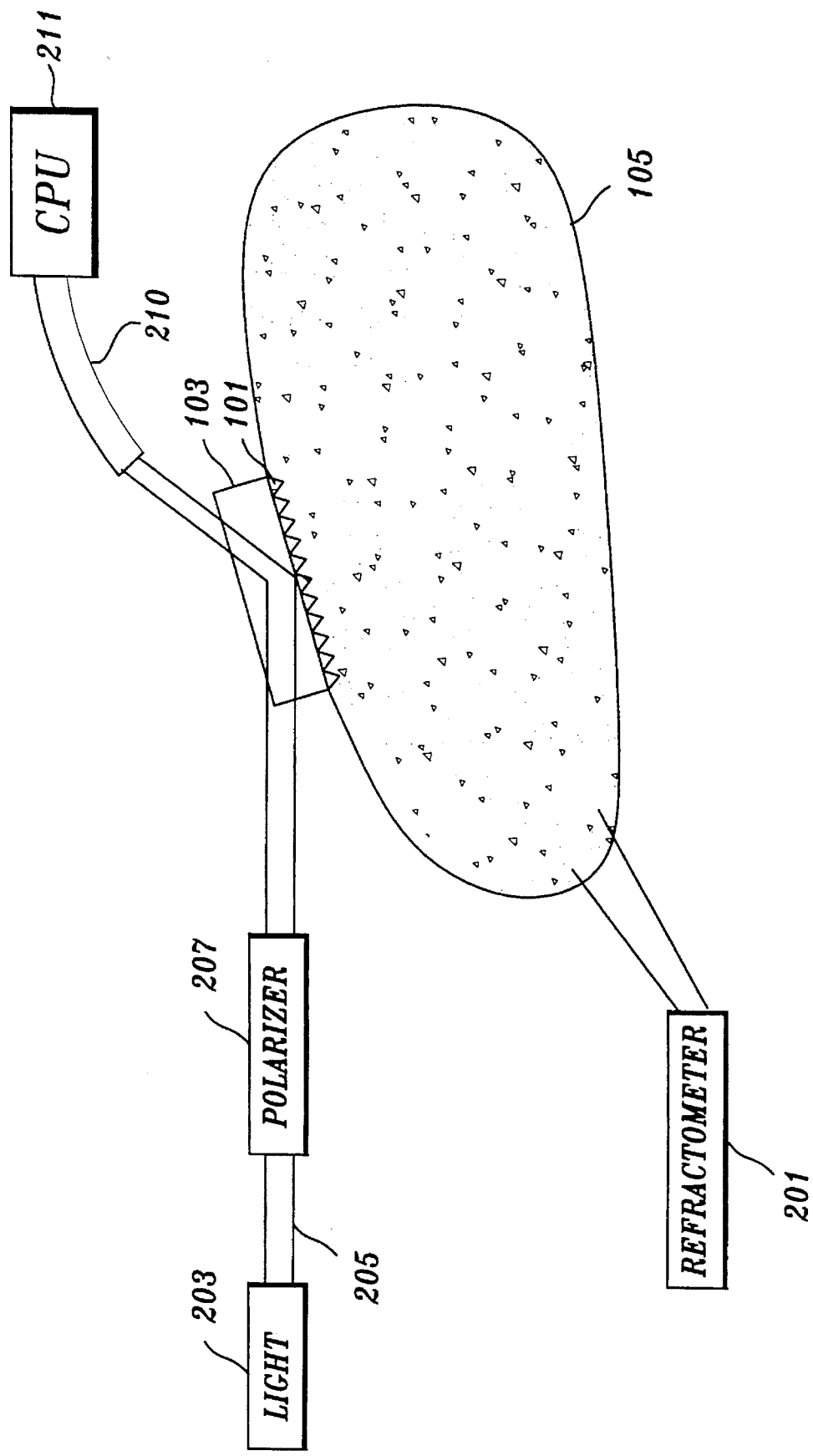

The relative ease of grating fabrication and also the ease with which this method can be coupled to a fiber optic allows for the integration of this sensor into a bulk optic that can be interrogated with an input fiber and an output fiber (210 in FIG. 1B). Also, the relative signal is high due to a single pass reflection measurement that does not undergo absorbance attenuation. Thus remote sensing with fiber optic coupling is achievable with this system.

The importance advantage of the proposed method is its versatility. The method may be employed in the light frequency range spanning from the UV to the mid IR, with wavelength selection determined by the grating period and angle of incidence. The potential here is for a single reflection method with sensitivity in the UV and visible to allow for spectral measurements of absorbance and refractive index in liquids and gases in a variety of environments.

While the preferred embodiment of the invention has been illustrated and described, it will be appreciated that various changes can be made therein without departing from the spirit and scope of the invention.

The embodiments of the invention in which an exclusive property or privilege is claimed are defined as follows:

1. An analytical sensor for determining the index of refraction of a liquid or gas, such sensor comprising:

a diffraction grating having a grating period formed on a dielectric and disposed in contact with said liquid or gas;

a polychromatic light source providing polychromatic light incident on said diffraction grating at an angle of incidence and wherein such incident light does not traverse said liquid or gas;

a detector array for capturing a reflection spectrum from said diffraction grating when said light is incident on said diffraction grating, said reflection spectrum including a diffraction order equal to zero; and a computer for determining said refractive index based upon at least said angle of incidence, said grating period, and said reflection spectrum.

2. The sensor of claim 1, wherein said polychromatic incident light is delivered by means of a fiber optic.

3. The sensor of claim 1, wherein said reflected light is captured by means of a fiber optic.

4. The sensor of claim 1, wherein said computer is capable of determining the composition of said liquid or gas based upon said refractive index.

5. The sensor of claim 3, further including a means for reproducing the spectrum of said reflected light after passing through said fiber optic and further including a means for measuring the spectrum so produced.

6. The sensor of claim 1, wherein said polychromatic incident light is delivered by means of fiber optics and said reflected light is captured by means of fiber optics.

7. A method for determining the index of refraction of a liquid or gas, said method comprising the steps of:

placing in contact with said liquid or gas a diffraction grating having a grating period formed on a dielectric;

illuminating said diffraction grating through the dielectric with polychromatic incident light at an angle of incidence and wherein said polychromatic incident light does not traverse said liquid or gas;

capturing a reflection spectrum including a diffraction order equal to zero from said diffraction grating when said polychromatic incident light is incident on said diffraction grating; and determining said refractive index based upon at least said angle of incidence, said grating period, and said reflection spectrum.

8. The method of claim 7, wherein said polychromatic incident light is delivered by means of fiber optics.

9. The method of claim 7, wherein said reflected light is captured by means of fiber optics.

10. The method of claim 7, further including the step of determining the composition of said liquid or gas based upon said refractive index.

11. The method of claim 9, further including the step of reproducing the spectrum of said reflected light after passing through said fiber optic and measuring the spectrum so produced.

12. An analytical sensor for determining the index of refraction of a liquid or a gas through phase measurement, said sensor comprising:

a diffraction grating having a grating period formed on a dielectric and disposed in contact with said liquid or gas;

a light source providing light incident on said diffraction grating at an angle of incidence and wherein such incident light does not pass through said liquid or gas;

a detector for capturing reflections from said diffraction grating and said dielectric when said light is incident on said diffraction grating and dielectric; and a computer for determining said refractive index through phase measurement based upon at least said angle of incidence, said grating period, and said reflections from said diffraction grating and said dielectric.

13. The sensor of claim 12, wherein said light is polarized light that is transverse electric.

14. The sensor of claim 12, wherein said light is polarized light that is transverse magnetic.

15. The sensor of claim 12, wherein said index of refraction is a complex quantity having real and imaginary parts.

16. The sensor of claim 12, wherein said detector for capturing said reflections is an array.

17. The sensor of claim 12, wherein said liquid or gas includes solid particulates suspended therein as a matrix.

18. The sensor of claim 12, wherein said incident light is delivered by means of fiber optics.

19. The sensor of claim 12, wherein said reflected light is captured by means of fiber optics.

20. A method for determining the index of refraction of a liquid or gas through phase measurement, said method comprising the steps of:

placing in contact with said liquid or gas a diffraction grating having a grating period formed on a dielectric;

illuminating said diffraction grating at an angle of incidence and wherein such incident light does not pass through said liquid or gas;

capturing reflections from said diffraction grating and dielectric when said light is incident on said diffraction grating and dielectric; and determining said refractive index through phase measurement based on at least said angle of incidence, said grating, and said reflections.

21. The method of claim 20, wherein said light is polarized light that is transverse electric.

22. The method of claim 20, wherein said light is polarized light that is transverse magnetic.

23. The method of claim 20, wherein said index of refraction is a complex quantity having real and imaginary parts.

24. The method of claim 20, wherein said reflections are captured by a detector array.

25. The method of claim 20, wherein said liquid or gas includes solid particulates suspended therein as a matrix.

26. The method of claim 20, wherein said incident light is delivered by means of fiber optics.

27. The method of claim 20, wherein said reflected light is captured by means of fiber optics.

28. The method of claim 20, wherein the composition of said liquid or gas is determined using said refractive index.

* * * * *

UNITED STATES PATENT AND TRADEMARK OFFICE
CERTIFICATE OF CORRECTION

PATENT NO. : 5,610,708
DATED : March 11, 1997
INVENTOR(S) : B. Anderson et al.

It is certified that error appears in the above-identified patent and that said Letters Patent is hereby corrected as shown below:

COLUMN  LINE

1  15  After "gases." insert --This invention was made with government support under grant number EEC84-15075 awarded by the National Science Foundation. The government has certain rights in the invention.--

Signed and Sealed this

Twenty-fifth Day of August, 1998

Attest:

BRUCE LEHMAN

Attesting Officer   Commissioner of Patents and Trademarks